(12) United States Patent
Bahiri et al.

(10) Patent No.: US 8,808,767 B2
(45) Date of Patent: Aug. 19, 2014

(54) NEMATODE CONTROL AGENT

(71) Applicants: Gidon Bahiri, Wisbech (GB); Ian Elliott, Normanby by Spital (GB)

(72) Inventors: Gidon Bahiri, Wisbech (GB); Ian Elliott, Normanby by Spital (GB)

(73) Assignee: Omex International Ltd., Hamilton (BM)

( * ) Notice: Subject to any disclaimer, the term of this patent is extended or adjusted under 35 U.S.C. 154(b) by 0 days.

(21) Appl. No.: 14/017,775

(22) Filed: Sep. 4, 2013

(65) Prior Publication Data

US 2014/0161914 A1 Jun. 12, 2014

Related U.S. Application Data

(63) Continuation of application No. 12/663,903, filed as application No. PCT/IB2008/052301 on Jun. 11, 2008, now abandoned.

(51) Int. Cl.
*A61K 36/8962* (2006.01)

(52) U.S. Cl.
USPC .......................................................... 424/754

(58) Field of Classification Search
None
See application file for complete search history.

(56) References Cited

U.S. PATENT DOCUMENTS

| | | | |
|---|---|---|---|
| 3,293,128 A | 12/1966 | Mann | |
| 3,781,301 A | 12/1973 | Nikles | |
| 4,059,615 A | 11/1977 | Weil | |
| 4,179,277 A | 12/1979 | Beck et al. | |
| 4,226,615 A | 10/1980 | Alt | |
| 4,309,422 A | 1/1982 | Stach et al. | |
| 4,584,318 A | 4/1986 | Peake | |
| 5,129,951 A | 7/1992 | Vaughn | |
| 6,720,352 B1 | 4/2004 | Rodriguez-Kabana | |
| 6,921,539 B2 | 7/2005 | Ninkov | |
| 2004/0082479 A1* | 4/2004 | Mirelman et al. | 504/349 |
| 2006/0078733 A1 | 4/2006 | Jassan et al. | |
| 2008/0194666 A1* | 8/2008 | Jabbour et al. | 514/408 |
| 2008/0255237 A1* | 10/2008 | McGee et al. | 514/574 |
| 2009/0317500 A1* | 12/2009 | Sadler-Bridge et al. | 424/754 |
| 2011/0218104 A1 | 9/2011 | Rodriguez-Kabana et al. | |

FOREIGN PATENT DOCUMENTS

| | | |
|---|---|---|
| JP | 07048208 A | 2/1995 |
| WO | 9956538 A | 11/1999 |
| WO | 0067577 A | 11/2000 |
| WO | 2005102024 A | 11/2005 |

OTHER PUBLICATIONS

Cinta, et al. Evaluation of natural chemical compounds against root-lesion and root-knot nematodes and side-effects on the infectivity of arbuscular mycorrhizal fungi. European Journal of Plant Pathology 107: 601-605, 2001.

Tsai, B.Y. A root-penetration bioassay for the screening of nematode-control principles. Journal Plant Pathology Bulletin 2000 vol. 9 No. 4 pp. 131-136.

Richer, D. L. Synergism—a patent view. Pesticide Science, vol. 19, Issue 4, pp. 309-315, 1987.

* cited by examiner

*Primary Examiner* — Chris R Tate
(74) *Attorney, Agent, or Firm* — Burns & Levinson LLP

(57) ABSTRACT

A composition for the control of nematodes consisting of salicylaldehyde and a surfactant. Garlic extract added to the salicylaldehyde provides a composition that demonstrates a more potent control action against potato cyst nematodes.

2 Claims, No Drawings

NEMATODE CONTROL AGENT

CROSS REFERENCE TO RELATED APPLICATIONS

This application is a continuation of U.S. patent application Ser. No. 12/663,903, which is a U.S. national phase application under 35 U.S.C. §371 of International Application No. PCT/IB2008/052301, filed on Jun. 11, 2008, which claims priority to and the benefit of United Kingdom Patent Application No. 0711065.3, filed on Jun. 11, 2007, the entire disclosures of each of which are incorporated by reference herein.

FIELD OF THE INVENTION

The present invention is in the field of agricultural pest control agents. More specifically the invention relates to such agents of biological source in their use as nematode control agents.

BACKGROUND OF THE INVENTION

Salicylaldehyde (SA) is a naturally occurring substance. In some plants and plant parts its concentration is considerable. It has been shown by Pasteels J M and J C Gregoire, 1983 (The chemical ecology of defense in Arthropods, Ann Rev Entomol 28:263-289) that larvae of the chrysomelid tribe Phaedomini secret salicylaldehyde. The salicylaldehyde is used as a natural repellent by the feeding beetle against small predators such as ants. The salicylaldehyde is produced by the larvae from salicin, a glucoside, which is extracted by the larvae from the host plant, and further used to produce salicylaldehyde by the feeding beetle.

In a previous invention by one of the co-inventors of the present invention, disclosed in PCT publication WO 2005/102024, the use of salicylaldehyde (SA) either alone or in combination with garlic extract, as control agent for diverse groups of pests was studied. In the present invention, sharing an inventor with the above cited invention, the potential use of SA as a nematode control agent was demonstrated.

DETAILED DESCRIPTION OF THE PRESENT INVENTION

Tests were performed by The Scottish Agricultural College (SAC) in Scotland, during the year 2006. Materials used in the tests were as follows: salicyladehyde mixed with the alcohol ethoxylate surfactant Symperonic 91-8, at 1:1 ratio, this mixture is referred to hereinafter as SAM. The surfactant was implemented in this case as a dispersant. Further agents used were garlic extract (GE), and GE mixed with SAM, at the ratio of 4:1. Such a mixture is hereinafter referred to as GASA (liquid). GASA was prepared also in the form of granules made by spraying the GASA on clay, as known in the art, the product contained about 5 liters of GASA for every 20 Kg final product (solid granules). Such granules are referred to hereinafter as GASA granules. Terpene, and Tyratech granules were also used in the experiments. All these materials were supplied by Omex Agriculture, of Bardney Airfield, Tupholme, Lincoln LN3 5TP, UK. In addition Vydate (oxamyl) granules were used as a standard nematicide treatment.

Experiment 1: Control of Potato Cyst Nematodes (PCN) (*Globodera rostochiensis*) in the Absence of Potato Tubers. These tests were carried to specifically measure the effect of soil treatments on the survival and viability of PCN cysts in the soil in the absence of any potato plants. All tests were carried out in glasshouses at SAC in Edinburgh. The plant pots with potatoes were initially kept outdoors for 1 month before moving indoors.

The pest: PCN (*G. rostochiensis*) cysts were obtained from the Scottish Agricultural Science Agency (SASA). They were obtained from their statutory sampling of fields for seed potato production in 2006. A sample of 5 cysts from the batch of cysts supplied by SASA was evaluated for viability and numbers of eggs/cyst. A mean count of $102.2\pm8.18$ eggs/cyst was found. After the experiments, PCN cysts were extracted from soil by drying the soil, crushing lightly with a roller, and then washing through sieves to collect the cysts through filtration. A sub-sample of the total cysts collected were split open to measure viability and to count the numbers of eggs or juvenile nematodes present, expressed as number of eggs/g of soil.

Soil: Soil used in the tests was obtained from a field at the Bush Estate which is routinely used for growing cereals. No potatoes have been grown in the field in living memory. Soil analysis indicated no PCN present in the soil, and very low numbers of free living nematodes. Soil was partially dried and crushed to ensure a fine-medium consistency for use in all of the pot tests.

Methodology: From the batch of PCN cysts obtained from SASA, 50 cysts were counted out and mixed with 250 g of soil for each replicate. The treatments were mixed with the 250 g of soil and 50 cysts and placed into small plastic pots. This gave an estimated baseline figure of $102.2/250 \times 50 = 20.44$ PCN eggs/g soil. The pots (15 per treatment) were watered every few days to keep moist but not saturated and were kept in a glasshouse at around 18° C.

After, approx 1 month (end of September), 2 months (end of October) and 3 months (end of November) all the soil from 5 pots from each treatment were extracted for PCN cysts. The viability of the cysts was assessed—i.e. how many cysts had live PCN eggs/larvae in them, and the mean No. of viable eggs/cyst was determined. This was then converted to the Mean No. of PCN eggs/g soil. The treatments and doses were as outlined below. As dose rates were supplied as ml/liter, they were converted to ml/kg assuming 1 kg of soil is equivalent to 1 liter.

Treatments: Control, GASA liquid at 2.5 ml/kg soil (as 250 g of soil used, 0.625 ml of the agent was mixed with the soil to get the equivalent rate). Terpene liquid at 2.5 ml/kg soil, GE at 2.5 ml/kg soil, GASA granules at 2.5 g/kg soil, Tyratech granules at 2.5 g/kg soil, SAM liquid at 1 ml/kg soil; Vydate (oxamyl) rate equivalent to 55 kg/ha. Each pot was 5 cm×5 cm=25 $cm^2$. i.e. 0.25 $m^2$. Vydate rate is equivalent to 5.5 $g/m^2$. So rate for each pot is $1/20^{th}$ of 5.5 $g/m^2=0.275$ g/pot Results: There was a decline in mean No. of eggs/g of soil over time in all treatments. This is to be expected as cysts will spontaneously hatch in the absence of potatoes (between 15-40% is usual), so it is the rate of decline that is important in these results. The Control pots have declined the least, going from 20.44 eggs/g at Time 0, to 18.67 eggs/g after one month, 17.86 eggs/g after two months and 16.47 eggs/g after 3 months. The GASA liquid treatment has caused the greatest decline in PCN eggs after 3 months, going from 20.44 eggs/g at Time 0, to 17.29 eggs/g after one month, 11.003 eggs/g after two months, and 5.14 eggs/g after 3 months. Differences in eggs/g of soil do not become apparent until 2 months exposure, when the following treatments have significantly fewer eggs/g of soil than the Control: GASA liquid (Analysis of variance, P<0.005), Terpene (P<0.05), GE (P<0.05) and Tyratech granules (P<0.05). The GASA liquid treatment also had significantly fewer eggs/g of soil than the Vydate and SAM treatments (P<0.05). After 3 months exposure, all treatments had significantly fewer eggs/g of soil than the Control and Vydate treatments (P<0.01). The GASA liquid treatment had significantly fewer eggs/g of soil than the Terpene (P<0.05), GE (P<0.005), GASA granules (P<0.05), Tyratech granules (P<0.001) and SAM (P<0.001) treatments. The GASA granules treatment had significantly fewer eggs/g of soil than the Tyratech granules (P<0.05) and SAM (P<0.01) treatments. The Terpene treatment had fewer eggs/g of soil than the SAM treatment (P<0.05). The decline in eggs/g of soil can be put down to a reduction in the viability of the PCN cysts over time and in response to the different treatments (see Table 1 below).

TABLE 1

Mean % of viable PCN cysts after exposure to various soil treatments

| Treatment | Mean % of viable PCN cysts (±SE) after: | | |
|---|---|---|---|
|  | 1 month | 2 months | 3 months |
| Control | 91.36 ± 2.61 | 87.38 ± 0.75 | 80.58 ± 2.78 |
| GASA liquid | 80.46 ± 1.71 | 53.83 ± 1.79 | 25.12 ± 6.79 |
| Terpene | 81.76 ± 3.72 | 65.40 ± 4.36 | 37.00 ± 7.14 |
| GE | 85.84 ± 4.64 | 62.12 ± 4.05 | 41.36 ± 3.01 |
| GASA granules | 85.58 ± 2.93 | 67.45 ± 4.92 | 34.30 ± 6.96 |
| Tyratech granules | 87.31 ± 3.59 | 66.13 ± 4.31 | 46.55 ± 3.50 |
| SAM | 84.10 ± 5.93 | 71.68 ± 5.51 | 52.32 ± 3.06 |
| Vydate | 86.96 ± 1.96 | 75.86 ± 3.05 | 84.38 ± 3.42 |

Only a quarter of the PCN cysts in the GASA liquid treatment were viable (i.e. contained live PCN eggs or juveniles) after 3 months exposure. The Control treatment still had 80% viable cysts after 3 months, as did the Vydate (oxamyl) standard nematicide treatment. All the other treatments did have an affect on PCN cyst viability to some extent, with the GASA Granules and the Terpene treatments reducing cyst viability to below 40%. Significant differences in PCN cyst viability became apparent between the GASA granules and Control treatments after 1 month (P<0.01), but it was not until the cysts had been exposed to the treatments for 2 months did differences in cyst viability between the Control and other treatments become significant (Table 1). All treatments had a significant decrease in cyst viability compared to the control after 2 months exposure: GASA liquid (P<0.001), GASA granules (P<0.005), Terpene (P<0.001), GE (P<0.001), Tyratech granules (P<0.001) and SAM (P<0.05). The Vydate treatment also had fewer viable cysts than the control treatment (P<0.01). The GASA liquid treatment had significantly fewer viable cysts than the Vydate (P<0.001), Terpene (P<0.05), GASA granules (P<0.05), Tyratech (P<0.05) and SAM (P<0.05) treatments after 2 months exposure. The GE treatment had significantly fewer viable cysts than the Vydate treatment after 2 months exposure (P<0.05). After 3 months, all treatments had a significant decrease in cyst viability compared to the control and Vydate treatments (P<0.001, Table 1). The GASA liquid treatment had significantly fewer viable cysts than the Tyratech (P<0.05) and SAM (P<0.05) treatments. The GE treatment and GASA granules treatment had significantly fewer viable cysts than the SAM treatment (P<0.05).

Summary: All treatments except Vydate reduced cyst viability to some extent compared to the Controll. Vydate (oxamyl) is a nematistat: i.e. the chemical paralyses the nematodes rather than killing them, and needs the nematodes to be liberated from the cysts in order to be effective. The other treatments applied to the soil appear to be able to have an impact on the nematodes within the cyst, suggesting that they are able to pass through the cyst wall or weaken the cyst to some extent. The GASA liquid and GASA granule treatments were the most effective at reducing PCN cyst viability. This was reflected in the numbers of eggs/g of soil for these treatments.

Experiment 2: Control of Potato Cyst Nematodes (PCN) (*Globodera rostochiensis*) in Soil with Potato Tubers.

Methodology: from the batch of PCN cysts obtained from SASA, 500 cysts were counted out and mixed with 2.5 kg of soil for each replicate. This gave the same PCN eggs/g count as in Experiment 1—20.44 eggs/g soil, which would be expected to cause a significant effect on yield if untreated. The treatments were mixed with the 2.5 kg of soil and 500 cysts and placed into large plastic pots. One seed tuber of the potato cultivar Cara was planted to a depth of 5 cm in each pot. For the liquid formulation treatments they were also applied as a soil drench 5 days post-planting. The pots were irrigated every few days to keep moist but not saturated and were initially kept outdoors for a month before moving into a glasshouse at around 18° C. The agents and doses were as outlined below. As dose rates were supplied as ml/liter, they were converted to ml/kg assuming 1 kg of soil is equivalent to 1 liter.

Treatments and agents: control with PCN cysts (10 replicates), control with no PCN cysts (10 replicates); GASA liquid at 2.5 ml/kg soil with PCN (as 2.5 kg of soil was used, 6.25 ml of the treatment was mixed with the soil to get the equivalent rate) (8 replicates); GASA liquid drench 5 days after planting at 2.5 ml/kg soil with PCN (since 2.5 kg of soil was used, a 6.25 ml portion was mixed in 100 ml of water and irrigated evenly over the soil surface to get the equivalent rate) (7 replicates); GE at 2.5 ml/kg soil with PCN (8 replicates). GE drench 5 days after planting at 2.5 ml/kg soil with PCN (7 replicates); GASA granules at 2.5 g/kg soil with PCN (10 replicates); Tyratech granules at 2.5 g/kg soil with PCN (10 replicates); SAM liquid at 1 ml/kg soil with PCN (7 replicates); SAM liquid drench 5 days after planting at 1 ml/kg soil with PCN (8 replicates); Vydate (oxamyl) rate equivalent to 55 kg/ha (2.75 g/pot) with PCN (10 replicates).

Plant height was recorded 20, 35, 45 and 60 days after planting. The potatoes were grown for 120 days to allow the life cycle of the PCN to be completed. No fungicides, herbicides, insecticides or fertiliser was applied to the potatoes. On day 117, the haulm of the potatoes was cut back. The pots were emptied onto white trays and the tubers produced by the roots were counted, removed, and washed to remove any soil before weighing. For each pot any tubers less than 2 cm in diameter were removed and not counted. After the potatoes had been removed, the soil from each pot was placed onto trays and dried. A sub-sample of 500 g of the soil from each pot was assessed for PCN egg counts. As the initial PCN eggs/g count was known at planting ($P_i$=20.44 eggs/g), the PCN eggs/g after harvest ($P_f$) was determined for each pot. The ratio of $P_f/P_i$ gives a measure of the rate of PCN multiplication for each pot.

Results: For several of the treatments (GASA liquid, GASA Granules, SAM, GE and Tyratech granules) there was transient yellowing of the foliage. The leaves eventually regained full green colour after 60 days. Most of the plants remained free of potato blight, although there were some occasional leaves affected towards the end of the trial.

Plant height: After 20 days, there are already significant differences between several treatments. All treatments were significantly taller than the control with PCN plants (Analysis of Variance, P<0.05). The GASA granules, GASA liquid and GE treated pots were significantly taller than the control without PCN (P<0.05). All of the experimental treatments were also significantly taller than the Vydate nematicide treatment (P<0.05). This may be indicative of a growth stimulation or fertiliser effect as PCN cyst hatch would be in its infancy at this stage. After 35 days, the plant height differences between the treatments are not so apparent, although all treatments have significantly taller plants than the control with PCN plants (P<0.01). Other differences in plant height are those between the GASA liquid and GASA liquid post planting drench (P<0.001) and the GE and GE post planting drench (P<0.05). After 45 days and 60 days, the only differences in plant height are those between all treatments and the Control with PCN (P<0.001), and the GASA liquid and GASA liquid post planting drench (P<0.01). The cumulative progress in plant height over time for all treatments shows that the GASA liquid, GASA granules and GE treatments have the most rapid rates of growth over the first 60 days.

Number of tubers: The number of tubers harvested after 120 days from all treatments is summarised in Table 2. Note that further tubers may well have been produced had the plants been grown for longer and in larger pots. The growth period of 120 days was chosen for the completion of the life cycle of PCN. There was great deal of variability within and between treatments in the number of tubers after 120 days (Table 2). The only significant difference in tuber number was between the control with PCN and the control with no PCN treatments (P<0.05), and the control with PCN and Vydate treatments (P<0.05).

Tuber yields: Mean tuber yields (total weight of all tubers) ranged from 83 g in the control with PCN pots to 110 g in the Vydate pots (Table 2). The following treatments has significantly greater yields than the Control with PCN pots: Vydate (P<0.001), control with no PCN (P<0.001), GASA liquid (P<0.05) and SAM post planting drench (P<0.05). The following treatments had a significantly less yield than the Vydate treatment: Control with PCN (P<0.001), GASA granules (P<0.05), GASA liquid post planting drench (P<0.05), GE (P<0.01), GE post planting drench (P<0.05), Tyratech granules (P<0.01) and SAM (P<0.05). In comparison with the control with no PCN yields, only GE and Tyratech granules had significantly reduced yields (P<0.05). The Vydate treatment having higher yields than some of the other treatments suggests that the nematodes are still able to feed and consequently reduce yields in those treatments, whilst the nematistatic action of Vydate paraylyses the majority of the nematodes resulting in higher yields.

TABLE 2

Mean number of potato tubers/pot and Mean yield of tubers/pot

| Treatment | Mean No. of tubers/pot (±SE) | Mean yield (total weight of tubers)/pot (±SE) |
| --- | --- | --- |
| Control with PCN | 5.70 ± 0.37 | 83.00 ± 3.65 |
| Control with no PCN | 7.00 ± 0.42 | 104.70 ± 4.41 |
| GASA Granules | 6.30 ± 0.50 | 91.8 ± 5.27 |
| GASA Liquid | 6.63 ± 0.60 | 98.13 ± 5.41 |
| GASA Liquid post drench | 5.86 ± 0.51 | 92.00 ± 4.60 |
| GE | 5.63 ± 0.50 | 88.25 ± 4.13 |
| GE post drench | 5.71 ± 0.57 | 90.43 ± 6.34 |
| Tyratech Granules | 5.90 ± 0.38 | 91.50 ± 3.64 |
| SAM | 6.29 ± 0.42 | 92.00 ± 5.01 |
| SAM post drench | 6.13 ± 0.44 | 97.38 ± 4.62 |
| Vydate | 7.20 ± 0.39 | 110.50 ± 5.27 |

PCN multiplication during the growing of the crop: The plants were grown for 120 days so that the life cycle of PCN on the roots of the potatoes could be completed—i.e new cysts formed. The mean number of PCN eggs/g soil extracted after harvest ($P_f$) is shown in Table 3. PCN multiplication in the Vydate, GASA granules and GASA liquid post planting drench treatments was approximately a third of that in the Control with PCN treatment (Table 3). The other treatments reduced PCN multiplication by approximately half compared to the Controll with PCN treatment (Table 3). The standard measure of PCN multiplication is the ratio of the final PCN population after harvest ($P_f$) to the initial PCN population at planting ($P_i$). The mean $P_f/P_i$ ratios are shown in Table 3.

TABLE 3

Mean No. of PCN eggs/g soil after harvest (Pf) and Mean rate of PCN multiplication ($P_f/P_i$) after harvest ($P_i$ = 20.44 eggs/g)

| Treatment | Mean No. of PCN eggs/g of soil ($P_f$) after harvest (±SE) | Mean PCN multiplication ($P_f/P_i$) after harvest (±SE) |
| --- | --- | --- |
| Control with PCN | 236.70 ± 17.80 | 11.58 ± 0.87 |
| GASA Granules | 76.00 ± 8.11 | 3.72 ± 0.40 |
| GASA Liquid | 69.25 ± 6.04 | 3.39 ± 0.30 |
| GASA Liquid. post drench | 113.57 ± 8.08 | 5.56 ± 0.40 |
| GE | 105.75 ± 8.92 | 5.17 ± 0.44 |
| GE. post drench | 126.86 ± 8.25 | 6.21 ± 0.40 |
| Tyratech Granules | 131.50 ± 8.22 | 6.43 ± 0.40 |
| SAM | 126.00 ± 10.40 | 6.16 ± 0.51 |
| SAM post drench | 155.50 ± 7.03 | 7.61 ± 0.34 |
| Vydate | 74.40 ± 6.83 | 3.64 ± 0.33 |

The mean $P_f/P_i$ ratios of all treatments were significantly lower than that of the Control with PCN treatment (P<0.001). The following treatments had a significantly lower $P_f/P_i$ ratio than the Vydate treatment: Control with PCN (P<0.001), GASA liquid post planting drench (P<0.05), GE (P<0.05), GE post planting drench (P<0.001), Tyratech granules (P<0.001), SAM (P<0.001), and SAM post planting drench (P<0.001). The following treatments had a significantly lower $P_f/P_i$ ratio than the GASA granules treatment: Control with PCN (P<0.001), GASA liquid post planting drench (P<0.01), GE (P<0.05), GE post planting drench (P<0.001), Tyratech granules (P<0.001), SAM (P<0.005), and SAM post planting drench (P<0.001). The following treatments had a significantly lower $P_f/P_i$ ratio than the GASA liquid treatment: Control with PCN (P<0.001), GASA liquid post planting drench (P<0.001), GE (P<0.005), GE post planting drench (P<0.001), Tyratech granules (P<0.001), SAM (P<0.001), and SAM post planting drench (P<0.001). The GASA liquid post planting drench had a significantly lower $P_f/P_i$ ratio than the SAM post planting drench treatment (P<0.005).

Summary: The treatments (apart from Vydate) stimulate plant growth to some extent, possibly due to nutrients present which act as a fertiliser enhance growth. Admixing treatments at planting with the soil was more effective at stimulating plant growth than a soil drench 5 days after planting. Tuber numbers are higher in the Vydate treatment, probably as a consequence of the Vydate being able to prevent the nematodes feeding due its nematistatic action. Tuber yields in the GASA liquid, GASA granules and GE post planting drench are comparable to that of Vydate. Vydate, GASA liquid and GASA granules have the most significant impact on PCN multiplication during the growing of the crop, suggesting that the GASA treatments have an impact on nematodes after they have hatched from cysts, either as a nematistat and/or by having a direct effect on nematode mortality.

Overall Summary

The GASA liquid and GASA granule treatments can reduce the viability of PCN cysts over a 3 month period when admixed with soil infested with PCN. Up to a 75% reduction in viability was seen, compared to a natural decline in viability of 20% in Control pots. The mechanism for this activity is not readily apparent. The chemicals in the GASA and other treatments may be able to pass through the cyst wall, may provide a food resource for naturally occurring bacteria and fungi in the soil to increase their populations and have an effect on the integrity of the cysts, may have a fumigant effect in the soil through when being broken down.

In the presence of potatoes, the treatments stimulate plant growth which may lead to the increased yield seen in some of the treatments. PCN multiplication does occur on the roots of treated plants, but for the GASA liquid and granule treatments in particular, is comparable to that obtained by the industry standard nematicide Vydate.

The invention claimed is:

1. A method of controlling soil nematodes in soil, the method comprising:
    applying to the soil a composition comprising effective amounts of salicylaldehyde, garlic extract, and a surfactant.

2. The method of claim 1, wherein the composition is a liquid.

* * * * *